United States Patent
Xu et al.

(10) Patent No.: US 10,238,771 B2
(45) Date of Patent: Mar. 26, 2019

(54) METHODS FOR TREATING BIOPROSTHETIC TISSUE USING A NUCLEOPHILE/ELECTROPHILE IN A CATALYTIC SYSTEM

(71) Applicant: Edwards Lifesciences Corporation, Irvine, CA (US)

(72) Inventors: Dengfeng Xu, Irvine, CA (US); Jeffrey S. Dove, Santa Ana, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 0 days.

(21) Appl. No.: 14/074,379

(22) Filed: Nov. 7, 2013

(65) Prior Publication Data

US 2014/0127804 A1     May 8, 2014

Related U.S. Application Data

(60) Provisional application No. 61/723,958, filed on Nov. 8, 2012.

(51) Int. Cl.
*A61L 27/36*     (2006.01)

(52) U.S. Cl.
CPC ....... *A61L 27/3687* (2013.01); *A61L 2400/02* (2013.01); *A61L 2430/40* (2013.01)

(58) Field of Classification Search
CPC ............. A61L 27/3687; A61L 2400/02; A61L 2430/20; A61L 27/507; A61L 27/3683; A61F 2/24; A61F 2210/0076; A61F 2/12; Y10S 623/92
USPC ........................................................ 435/375
See application file for complete search history.

(56) References Cited

U.S. PATENT DOCUMENTS

| | | |
|---|---|---|
| 2,393,580 A | 1/1946 | Weiskopf |
| 2,484,813 A | 10/1949 | Bower |
| 2,567,929 A | 9/1951 | Fessenden |
| 3,002,895 A | 10/1961 | Freedman |
| 3,093,439 A | 6/1963 | Bothwell |
| 3,870,789 A | 3/1975 | Mikat |
| 3,927,422 A | 12/1975 | Sawyer |
| 3,961,097 A | 6/1976 | Gravlee, Jr. |
| 3,966,401 A | 6/1976 | Hancock et al. |
| 4,050,893 A | 9/1977 | Hancock et al. |
| 4,067,091 A | 1/1978 | Backman |
| 4,082,507 A | 4/1978 | Sawyer |
| 4,120,649 A | 10/1978 | Schechter |
| 4,120,991 A | 10/1978 | Ornstein et al. |
| 4,207,689 A | 6/1980 | Romera-Sierra et al. |
| 4,294,753 A | 10/1981 | Urist |
| 4,320,157 A | 3/1982 | von Hagens |
| 4,323,358 A | 4/1982 | Lentz et al. |
| 4,328,256 A | 5/1982 | Romero-Sierra et al. |
| 4,347,671 A | 9/1982 | Dias et al. |
| 4,350,492 A | 9/1982 | Wright et al. |
| 4,372,743 A | 2/1983 | Lane |
| 4,378,224 A | 3/1983 | Nimni et al. |
| 4,402,697 A | 9/1983 | Pollock et al. |
| 4,405,327 A | 9/1983 | Pollock |
| 4,481,009 A | 11/1984 | Nashef |
| 4,553,974 A | 11/1985 | Dewanjee |
| 4,599,084 A | 7/1986 | Nashef |
| 4,624,822 A | 11/1986 | Arru et al. |
| 4,647,283 A | 3/1987 | Carpentier et al. |
| 4,648,881 A | 3/1987 | Carpentier et al. |
| 4,655,773 A | 4/1987 | Grassi |
| 4,676,070 A | 6/1987 | Linner |
| 4,729,139 A | 3/1988 | Nashef |
| 4,729,766 A | 3/1988 | Bergentz et al. |
| 4,753,652 A | 6/1988 | Langer et al. |
| 4,758,151 A | 7/1988 | Arru et al. |
| 4,770,665 A | 9/1988 | Nashef |
| 4,776,853 A | 10/1988 | Klement et al. |
| 4,786,287 A | 11/1988 | Nashef et al. |
| 4,793,344 A | 12/1988 | Cumming et al. |
| 4,800,603 A | 1/1989 | Jaffe |
| 4,831,065 A | 5/1989 | Pietsch et al. |
| 4,838,888 A | 6/1989 | Nashef |
| 4,865,871 A | 9/1989 | Livesey et al. |
| 4,885,005 A | 12/1989 | Nashef et al. |
| 4,891,319 A | 1/1990 | Roser |
| 4,911,713 A | 3/1990 | Sauvage et al. |
| 4,958,008 A | 9/1990 | Petite et al. |
| 4,969,912 A | 11/1990 | Kelman et al. |
| 4,975,526 A | 12/1990 | Kuberasampath et al. |
| 4,976,733 A | 12/1990 | Girardot |
| 4,990,131 A | 2/1991 | Dardik et al. |
| 4,994,030 A | 2/1991 | Glowczewskie, Jr. et al. |
| 4,994,237 A | 2/1991 | Login et al. |
| 4,996,054 A | 2/1991 | Pietsch et al. |
| 5,002,566 A | 3/1991 | Carpentier et al. |

(Continued)

FOREIGN PATENT DOCUMENTS

| | | |
|---|---|---|
| EP | 0169259 A1 | 1/1986 |
| WO | 84/01894 A1 | 5/1984 |

(Continued)

OTHER PUBLICATIONS

Steinmetz et al. The broad scope of cesium salts. Organic Chemistry. 2011;1-12.*

(Continued)

*Primary Examiner* — Lynn Y Fan
(74) *Attorney, Agent, or Firm* — Michelle C. Kim; Darren M. Franklin; Sheppard, Mullin, Richter & Hampton LLP (57) ABSTRACT

Methods for treating a bioprosthetic tissue are described herein. The methods comprise contacting the bioprosthetic tissue with at least one nucleophile and/or at least one electrophile in the presence of a catalytic system comprising at least one or a combination of a fluoride-based salt, a cesium-based salt, a potassium-based salt, a rubidium-based salt, or a carbonate-based salt. The methods may be used to alter functional groups on biological tissue which represent actual and potential calcium binding sites and also processes for cross-linking bioprosthetic tissue. Both processes may be used in conjunction with known fixative techniques, such as glutaraldehyde fixation, or may be used to replace known fixative techniques.

17 Claims, 2 Drawing Sheets

(56) References Cited

U.S. PATENT DOCUMENTS

| | | |
|---|---|---|
| 5,011,494 A | 4/1991 | von Recum et al. |
| 5,011,913 A | 4/1991 | Benedict et al. |
| 5,024,830 A | 6/1991 | Linner |
| 5,044,165 A | 9/1991 | Linner et al. |
| 5,051,401 A | 9/1991 | Sikes |
| 5,068,086 A | 11/1991 | Sklenak et al. |
| 5,068,100 A | 11/1991 | McClanahan |
| 5,080,670 A | 1/1992 | Imamura et al. |
| 5,094,661 A | 3/1992 | Levy et al. |
| 5,104,405 A | 4/1992 | Nimni |
| 5,108,923 A | 4/1992 | Benedict et al. |
| 5,116,564 A | 5/1992 | Jansen et al. |
| 5,131,908 A | 7/1992 | Dardik et al. |
| 5,147,514 A | 9/1992 | Mechanic |
| 5,149,621 A | 9/1992 | McNally et al. |
| 5,149,653 A | 9/1992 | Roser |
| 5,154,007 A | 10/1992 | Piunno et al. |
| 5,163,955 A | 11/1992 | Love et al. |
| 5,200,399 A | 4/1993 | Wettlaufer et al. |
| 5,215,541 A | 6/1993 | Nashef et al. |
| 5,275,954 A | 1/1994 | Wolfinbarger et al. |
| 5,279,612 A | 1/1994 | Eberhardt |
| 5,288,288 A | 2/1994 | Lewis et al. |
| 5,290,558 A | 3/1994 | O'Leary et al. |
| 5,296,583 A | 3/1994 | Levy |
| 5,329,846 A | 7/1994 | Bonutti |
| 5,332,475 A | 7/1994 | Mechanic |
| 5,336,616 A | 8/1994 | Livesey et al. |
| 5,368,608 A | 11/1994 | Levy et al. |
| 5,397,353 A | 3/1995 | Oliver et al. |
| 5,424,047 A | 6/1995 | Zwingenberger et al. |
| 5,436,291 A | 7/1995 | Levy et al. |
| 5,437,287 A | 8/1995 | Phillips et al. |
| 5,447,536 A | 9/1995 | Girardot et al. |
| 5,447,724 A | 9/1995 | Helmus et al. |
| 5,460,962 A | 10/1995 | Kemp |
| 5,476,516 A | 12/1995 | Seifter et al. |
| 5,507,813 A | 4/1996 | Dowd et al. |
| 5,509,932 A | 4/1996 | Keogh et al. |
| 5,554,184 A | 9/1996 | Machiraju |
| 5,556,379 A | 9/1996 | Wolfinbarger |
| 5,558,875 A | 9/1996 | Wang |
| 5,595,571 A | 1/1997 | Jaffe et al. |
| 5,613,982 A | 3/1997 | Goldstein |
| 5,632,778 A | 5/1997 | Goldstein |
| 5,645,587 A | 7/1997 | Chanda et al. |
| 5,674,298 A | 10/1997 | Levy et al. |
| 5,679,112 A | 10/1997 | Levy et al. |
| 5,695,820 A | 12/1997 | Davis et al. |
| 5,697,972 A | 12/1997 | Kim et al. |
| 5,713,953 A | 2/1998 | Vallana et al. |
| 5,716,399 A | 2/1998 | Love |
| 5,720,777 A | 2/1998 | Jaffe et al. |
| 5,720,894 A | 2/1998 | Neev et al. |
| 5,733,339 A | 3/1998 | Girardot et al. |
| 5,746,775 A | 5/1998 | Levy et al. |
| 5,762,600 A | 6/1998 | Bruchman et al. |
| 5,766,520 A | 6/1998 | Bronshtein |
| 5,769,780 A | 6/1998 | Hata et al. |
| 5,770,193 A | 6/1998 | Vacanti et al. |
| 5,773,285 A | 6/1998 | Park |
| 5,776,182 A | 7/1998 | Bruchman et al. |
| 5,782,914 A | 7/1998 | Schankereli |
| 5,782,915 A | 7/1998 | Stone |
| 5,782,931 A | 7/1998 | Yang et al. |
| 5,792,603 A | 8/1998 | Dunkelman et al. |
| 5,843,180 A | 12/1998 | Jaffe et al. |
| 5,843,181 A | 12/1998 | Jaffe et al. |
| 5,843,182 A | 12/1998 | Goldstein |
| 5,855,620 A | 1/1999 | Bishopric et al. |
| 5,856,102 A | 1/1999 | Bierke-Nelson et al. |
| 5,856,172 A | 1/1999 | Greenwood et al. |
| 5,862,806 A | 1/1999 | Cheung |
| 5,865,849 A | 2/1999 | Stone |
| 5,873,812 A | 2/1999 | Ciana et al. |
| 5,879,383 A | 3/1999 | Bruchman et al. |
| 5,882,850 A | 3/1999 | Khor et al. |
| 5,882,918 A | 3/1999 | Goffe |
| 5,899,936 A | 5/1999 | Goldstein |
| 5,902,338 A | 5/1999 | Stone |
| 5,904,718 A | 5/1999 | Jefferies |
| 5,911,951 A | 6/1999 | Girardot et al. |
| 5,913,900 A | 6/1999 | Stone |
| 5,919,472 A | 7/1999 | Trescony et al. |
| 5,921,980 A | 7/1999 | Kirn |
| 5,922,027 A | 7/1999 | Stone |
| 5,931,969 A | 8/1999 | Carpentier et al. |
| 5,935,168 A | 8/1999 | Yang et al. |
| 5,945,319 A | 8/1999 | Keogh |
| 5,977,153 A | 11/1999 | Camiener |
| 5,987,720 A | 11/1999 | Yamamoto |
| 5,993,844 A | 11/1999 | Abraham et al. |
| 6,008,292 A | 12/1999 | Lee et al. |
| 6,017,741 A | 1/2000 | Keogh |
| 6,024,735 A | 2/2000 | Wolfinbarger, Jr. |
| 6,039,726 A | 3/2000 | Lewis et al. |
| 6,063,120 A | 5/2000 | Stone |
| 6,066,160 A | 5/2000 | Colvin et al. |
| 6,086,580 A | 7/2000 | Mordon et al. |
| 6,093,204 A | 7/2000 | Stone |
| 6,093,530 A | 7/2000 | McIlroy et al. |
| 6,106,555 A | 8/2000 | Yang |
| 6,117,979 A | 9/2000 | Hendriks et al. |
| 6,121,041 A | 9/2000 | Mirsch, II et al. |
| 6,126,686 A | 10/2000 | Badylak et al. |
| 6,129,758 A | 10/2000 | Love |
| 6,132,472 A | 10/2000 | Bonutti |
| 6,132,473 A | 10/2000 | Williams et al. |
| 6,132,986 A | 10/2000 | Pathak et al. |
| 6,156,030 A | 12/2000 | Neev |
| 6,156,531 A | 12/2000 | Pathak et al. |
| 6,165,215 A | 12/2000 | Rottenberg et al. |
| 6,166,184 A | 12/2000 | Hendriks et al. |
| 6,174,331 B1 | 1/2001 | Moe et al. |
| 6,177,514 B1 | 1/2001 | Pathak et al. |
| 6,190,407 B1 | 2/2001 | Ogle et al. |
| 6,193,749 B1 | 2/2001 | Schroeder et al. |
| 6,203,755 B1 | 3/2001 | Odland |
| 6,206,873 B1 | 3/2001 | Paolini et al. |
| 6,206,917 B1 | 3/2001 | Williams et al. |
| 6,210,957 B1 | 4/2001 | Carpentier et al. |
| 6,214,054 B1 | 4/2001 | Cunanan et al. |
| 6,214,055 B1 | 4/2001 | Simionescu et al. |
| 6,231,608 B1 | 5/2001 | Stone |
| 6,231,614 B1 | 5/2001 | Yang |
| 6,251,579 B1 | 6/2001 | Moore et al. |
| 6,254,635 B1 | 7/2001 | Schroeder et al. |
| 6,258,320 B1 | 7/2001 | Persing et al. |
| 6,267,786 B1 | 7/2001 | Stone |
| 6,277,555 B1 | 8/2001 | Duran et al. |
| 6,287,338 B1 | 9/2001 | Sarnowski et al. |
| 6,290,991 B1 | 9/2001 | Roser et al. |
| 6,302,909 B1 | 10/2001 | Ogle et al. |
| 6,312,474 B1 | 11/2001 | Francis et al. |
| 6,322,593 B1 | 11/2001 | Pathak et al. |
| 6,322,994 B1 | 11/2001 | Reid |
| 6,328,762 B1 | 12/2001 | Anderson et al. |
| 6,334,873 B1 | 1/2002 | Lane et al. |
| 6,352,708 B1 | 3/2002 | Duran et al. |
| 6,364,905 B1 | 4/2002 | Simpson et al. |
| 6,372,228 B1 | 4/2002 | Gregory |
| 6,375,680 B1 | 4/2002 | Carlyle |
| 6,376,244 B1 | 4/2002 | Atala |
| 6,383,732 B1 | 5/2002 | Stone |
| 6,391,538 B1 | 5/2002 | Vyavahare et al. |
| 6,394,096 B1 | 5/2002 | Constantz |
| 6,448,076 B2 | 9/2002 | Dennis et al. |
| 6,468,660 B2 | 10/2002 | Ogle et al. |
| 6,471,723 B1 | 10/2002 | Ashworth et al. |
| 6,479,079 B1 | 11/2002 | Pathak et al. |
| 6,482,199 B1 | 11/2002 | Neev |
| 6,506,339 B1 | 1/2003 | Girardot et al. |
| 6,509,145 B1 | 1/2003 | Torrianni |
| 6,527,979 B2 | 3/2003 | Constantz et al. |

(56) References Cited

U.S. PATENT DOCUMENTS

| | | |
|---|---|---|
| 6,528,006 B1 | 3/2003 | Jansen |
| 6,531,310 B1 | 3/2003 | Mirsch, II et al. |
| 6,534,004 B2 | 3/2003 | Chen et al. |
| 6,547,827 B2 | 4/2003 | Carpentier et al. |
| 6,561,970 B1 | 5/2003 | Carpentier et al. |
| 6,569,200 B2 | 5/2003 | Wolfinbarger, Jr. et al. |
| 6,582,464 B2 | 6/2003 | Gabbay |
| 6,586,006 B2 | 7/2003 | Roser et al. |
| 6,586,573 B1 | 7/2003 | Besman et al. |
| 6,589,591 B1 | 7/2003 | Mansouri et al. |
| 6,605,079 B2 | 8/2003 | Shanks et al. |
| 6,605,667 B1 | 8/2003 | Badejo et al. |
| 6,613,278 B1 | 9/2003 | Mills et al. |
| 6,617,142 B2 | 9/2003 | Keogh et al. |
| 6,630,001 B2 | 10/2003 | Duran et al. |
| 6,652,594 B2 | 11/2003 | Francis et al. |
| 6,653,062 B1 | 11/2003 | DePablo et al. |
| 6,660,265 B1 | 12/2003 | Chen et al. |
| 6,676,654 B1 | 1/2004 | Balle-Petersen et al. |
| 6,676,655 B2 | 1/2004 | McDaniel |
| 6,682,559 B2 | 1/2004 | Myers et al. |
| 6,685,940 B2 | 2/2004 | Andya et al. |
| 6,696,074 B2 | 2/2004 | Dai et al. |
| 6,734,018 B2 | 5/2004 | Wolfinbarger, Jr. et al. |
| 6,753,181 B2 | 6/2004 | Atala |
| 6,790,229 B1 | 9/2004 | Berreklouw |
| 6,797,000 B2 | 9/2004 | Simpson et al. |
| 6,828,310 B2 | 12/2004 | Barresi et al. |
| 6,872,226 B2 | 3/2005 | Cali et al. |
| 6,878,168 B2 | 4/2005 | Carpentier et al. |
| 6,893,666 B2 | 5/2005 | Spievack |
| 6,908,591 B2 | 6/2005 | MacPhee et al. |
| 6,911,043 B2 | 6/2005 | Myers et al. |
| 6,919,172 B2 | 7/2005 | DePablo et al. |
| 6,933,326 B1 | 8/2005 | Griffey et al. |
| 6,939,378 B2 | 9/2005 | Fishman et al. |
| 7,008,763 B2 | 3/2006 | Cheung |
| 7,022,119 B2 | 4/2006 | Hohla |
| 7,037,333 B2 | 5/2006 | Myers et al. |
| 7,063,726 B2 | 6/2006 | Crouch et al. |
| 7,078,163 B2 | 7/2006 | Torrianni |
| 7,087,723 B2 | 8/2006 | Besman et al. |
| 7,141,064 B2 | 11/2006 | Scott et al. |
| 7,143,769 B2 | 12/2006 | Stoltz et al. |
| 7,147,846 B2 | 12/2006 | Anderson et al. |
| 7,217,265 B2 | 5/2007 | Hennings et al. |
| 7,238,200 B2 | 7/2007 | Lee et al. |
| 7,318,998 B2 | 1/2008 | Goldstein et al. |
| 7,338,757 B2 | 3/2008 | Wolfinbarger, Jr. et al. |
| 7,354,749 B2 | 4/2008 | Fisher et al. |
| 7,358,284 B2 | 4/2008 | Griffey et al. |
| 7,367,969 B2 | 5/2008 | Stoltz et al. |
| 7,498,565 B2 | 3/2009 | Silberberg et al. |
| 7,594,974 B2 | 9/2009 | Cali et al. |
| 7,648,676 B2 | 1/2010 | Mills et al. |
| 7,682,304 B2 | 3/2010 | Heyninck-Jantz et al. |
| 7,871,434 B2 | 1/2011 | Case et al. |
| 7,914,569 B2 | 3/2011 | Nguyen et al. |
| 7,919,112 B2 | 4/2011 | Pathak et al. |
| 7,963,958 B2 | 6/2011 | Stoltz et al. |
| 7,972,376 B1 | 7/2011 | Dove et al. |
| 8,043,450 B2 | 10/2011 | Cali et al. |
| 8,075,615 B2 | 12/2011 | Eberhardt et al. |
| 8,136,218 B2 | 3/2012 | Millwee et al. |
| 2001/0000804 A1 | 5/2001 | Goldstein et al. |
| 2001/0020191 A1 | 9/2001 | Williams et al. |
| 2001/0025196 A1 | 9/2001 | Chinn et al. |
| 2001/0027344 A1 | 10/2001 | Bonutti |
| 2001/0032024 A1 | 10/2001 | Cunanan et al. |
| 2001/0039459 A1 | 11/2001 | Stone |
| 2002/0001834 A1 | 1/2002 | Keogh et al. |
| 2002/0049498 A1 | 4/2002 | Yuksel et al. |
| 2002/0091441 A1 | 7/2002 | Guzik |
| 2002/0111532 A1 | 8/2002 | Pathak et al. |
| 2003/0035843 A1 | 2/2003 | Livesey et al. |
| 2003/0125805 A1 | 7/2003 | Johnson et al. |
| 2003/0135284 A1 | 7/2003 | Crouch et al. |
| 2003/0167089 A1 | 9/2003 | Lane |
| 2003/0212454 A1 | 11/2003 | Scott et al. |
| 2004/0030381 A1 | 2/2004 | Shu |
| 2004/0086543 A1 | 5/2004 | Keogh et al. |
| 2004/0158320 A1 | 8/2004 | Simionescu et al. |
| 2004/0193259 A1 | 9/2004 | Gabbay |
| 2005/0010773 A1 | 1/2005 | Lapstun et al. |
| 2005/0024460 A1 | 2/2005 | McNally et al. |
| 2005/0059800 A1* | 3/2005 | Sudhakar et al. ............ 530/331 |
| 2005/0079200 A1 | 4/2005 | Rathenow et al. |
| 2005/0119736 A1 | 6/2005 | Zilla et al. |
| 2005/0136510 A1 | 6/2005 | Hendriks et al. |
| 2005/0211680 A1 | 9/2005 | Li et al. |
| 2005/0244069 A1* | 11/2005 | Alferiev et al. ............ 424/426 |
| 2006/0084957 A1 | 4/2006 | Delfyett et al. |
| 2006/0099326 A1 | 5/2006 | Keogh et al. |
| 2006/0110370 A1 | 5/2006 | Pathak et al. |
| 2006/0159641 A1 | 7/2006 | Girardot et al. |
| 2006/0177426 A1 | 8/2006 | Gibson et al. |
| 2006/0210960 A1 | 9/2006 | Livesey et al. |
| 2006/0217804 A1 | 9/2006 | Dove |
| 2006/0217805 A1 | 9/2006 | Dove |
| 2006/0228391 A1 | 10/2006 | Seyedin et al. |
| 2007/0010804 A1 | 1/2007 | Rathjen et al. |
| 2007/0048340 A1 | 3/2007 | Ferren et al. |
| 2007/0050014 A1 | 3/2007 | Johnson |
| 2007/0073392 A1 | 3/2007 | Heyninck-Jantz et al. |
| 2007/0203576 A1 | 8/2007 | Lee et al. |
| 2007/0254005 A1 | 11/2007 | Pathak et al. |
| 2007/0292459 A1 | 12/2007 | Cooper et al. |
| 2008/0195123 A1 | 8/2008 | Gainor et al. |
| 2008/0302372 A1* | 12/2008 | Davidson et al. ............ 128/898 |
| 2009/0041729 A1 | 2/2009 | Wolfinbarger, Jr. et al. |
| 2009/0112309 A1 | 4/2009 | Jaramillo et al. |
| 2009/0118716 A1 | 5/2009 | Brownell |
| 2009/0130162 A2 | 5/2009 | Pathak et al. |
| 2009/0137999 A1 | 5/2009 | Silberberg et al. |
| 2009/0164005 A1 | 6/2009 | Dove et al. |
| 2009/0188900 A1 | 7/2009 | Cali et al. |
| 2009/0281530 A1 | 11/2009 | Korn |
| 2009/0326524 A1 | 12/2009 | Cali et al. |
| 2010/0036484 A1 | 2/2010 | Hariton et al. |
| 2010/0100084 A1 | 4/2010 | Girard et al. |
| 2011/0028957 A1 | 2/2011 | Raksi et al. |
| 2011/0092966 A1 | 4/2011 | Guo et al. |
| 2011/0118609 A1 | 5/2011 | Goldshleger et al. |
| 2011/0165675 A1 | 7/2011 | Dove et al. |
| 2011/0177150 A1 | 7/2011 | Pathak et al. |
| 2011/0238167 A1 | 9/2011 | Dove et al. |
| 2011/0295363 A1 | 12/2011 | Girard et al. |
| 2012/0035720 A1 | 2/2012 | Cali et al. |
| 2012/0059487 A1 | 3/2012 | Cunanan et al. |
| 2012/0067855 A1 | 3/2012 | Guo et al. |
| 2012/0328905 A1 | 12/2012 | Guo et al. |

FOREIGN PATENT DOCUMENTS

| | | | |
|---|---|---|---|
| WO | 9009102 A1 | 8/1990 | |
| WO | WO9009102 * | 8/1990 | ............... A01N 1/02 |
| WO | 95/11047 A1 | 4/1995 | |
| WO | 95/022361 A1 | 8/1995 | |
| WO | 95/034332 A1 | 12/1995 | |
| WO | 96/004028 A1 | 2/1996 | |
| WO | 96/013227 A1 | 5/1996 | |
| WO | 98007452 A1 | 2/1998 | |
| WO | 98043556 A1 | 10/1998 | |
| WO | 00/032252 A1 | 6/2000 | |
| WO | 03/037227 A2 | 5/2003 | |
| WO | 04/082536 A1 | 9/2004 | |
| WO | 2006/026325 A2 | 3/2006 | |
| WO | 2006/099334 A2 | 9/2006 | |

OTHER PUBLICATIONS

Invitrogen. Thermo Fisher Scientific. Crosslinking and photoactivatable reagents. 2010;171-188.*

(56) References Cited

OTHER PUBLICATIONS

Parenteau-Bareil et al. Collagen-based biomaterials for tissue engineering applications. Materials. 2010;3:1863-1887.*

Al-Fagih, M.R., et al., "Aortic Valve Repair Using Bovine Pericardium for Cusp Extenstion," Journal of Thoracic and Cardiovascular Surgery, vol. 9, No. 5, pp. 760-764, 7988.

Carpentier, A., et al., "Biological Factors Affecting Long-Term Results of Valvular Heterografts," Forty-ninth Meeting of the American Assoication for Thoracic Surgery, San Francisco, CA, Mar. 31-Apr. 2, 1969.

Chanda, J., et al., "Heparin in Calcification Prevention of Porcine Pericardial Bioprostheses," Biomaterials, Elsevier Science Publishers, vol. 18, No. 16, ISSN: 0142-9612, Aug. 1, 1997.

Chvapil, M., et al., "Use of Chemically Purified and Cross-Linked Bovine Pericardium as a Ligament Substitute," Journal of Biomedical Materials Research, vol. 21, No. 12, pp. 1383-1394, 1987, University of Arizona Health Science Center, Tucson, AZ.

Dahm, Manfred, et al., "Effects of Surface Seeding with Vital Cells on the Calcium Uptake of Biological Materials for Heart Valve Replacement," J Heart Valve dis, Vole. 5, No. 2, Mar. 1996, pp. 148-151.

Fanner, P., et al., "Systematic Review of Preservation Methods and Clinical Outcome of Infrainguinal Vascular Allografts," Jounral of Vascular Surgery, vol. 44, No. 3, pp. 518-524, 2006.

Fumoto, H., et al., "Performance of Bioprosthetic Valves After Glycerol Dehydration, Ethylene Oxide Sterilization, and Rehydration," Innovations, vol. 6, No. 1, Jan./ Feb. 2011.

Grant, R.A., et al., "The Effects of Irradiation with High Energy Electrons on the Structure and Reactivity of Native and Cross-Linked Collagen Fibres," J. Cell Sci. vol. 7, 99. 387-405, 1970.

Hauschka, P., et al., "Direct Identification of the Calcium-Binding Amino Acid, y-Carboxyglutamate, in Mineralized Tissue," Proc. nat. Acas. Sci, vol. 72, No. 10, pp. 3925-3929, Oct. 1975.

International Search Report from corresponding PCT Case No. PCT/US2011/029654 dated Dec. 23, 2011.

Jayakrishnan, A., et al., "Glutaraldehyde as a Fixative in Bioprostheses and Drug Delivery Matrices," Biomaterials, vol. 17, Issue 5, 1995, pp. 471-484.

Khor, Eugene, "Methods for the Treatment of Collagenous Tissues for Bioprostheses," Biomaterials, vol. 18, Issue 2, Jan. 1997, pp. 95-105.

Ohan, M., et al., "Glucose Stabilizes Collagen Sterilized with Gamma Irradiation," Wiley Periodicals, Inc., pp. 1188-1195, 2003.

Olde Damink, L.H.H., et al., "Influence of Ethylene Oxide Gas Treatment on the in vitro Degradation Behavior of Dermal Sheep Collagen," Journal of Biomedical Materials Resaerch, vol. 29, pp. 149-155, 1995.

Parker, R., et al., "Storage of Heart Valve Allografts in Glycerol with Subsequent Antibiotic Sterilization," Thorax, British Thoracic Society, vol. 33, No. 5, pp. 638-645, 1978.

Saegeman, V., et al., "Short and long term bacterial inhibiting effect of high concentrations of glycerol used in the prevention of skin allografts," Science Direct, Burns, No. 34, Mar. 2008.

Schmidt, C., et al., "Acellular Vascular Tissues: Natural Biomaterials for Tissue Repair and Tissue Engineering," Biomaterials, vol. 21, pp. 2215-2231, 2000.

Zilla, P., et al., "Carbodiimide Treatment Dramatically Potentiates the Anticalcific Effect of Alpha-Amino Oleic Acid on Glutaraldehyde-Fixed Aortic Wall Tissue," The Annals of Thoracic Surgery, Elsevier, vol. 79, No. 3, ISSN: 0003-4975; Mar. 1, 2005.

International Search Report from Corresponding PCT Application No. PCT/US2013/069230, dated Feb. 12, 2014.

Acros Organics: "Catalysts Cesium Contents", Nov. 5, 2006 (Nov. 5, 2006), XP055528926, retrieved from the Internet: URL:https://www.acros.com/_Rainbow/pdf/brochure_cesium_v2.pdf [retrieved on Nov. 30, 2018].

* cited by examiner

METHODS FOR TREATING BIOPROSTHETIC TISSUE USING A NUCLEOPHILE/ELECTROPHILE IN A CATALYTIC SYSTEM

CROSS-REFERENCE TO RELATED APPLICATIONS

This application claims the benefit of priority under 35 U.S.C. § 119(e) to U.S. Provisional Patent Application Ser. No. 61/723,958, filed on Nov. 8, 2012, the entire contents of which are incorporated by reference as if fully set forth herein.

FIELD OF THE INVENTION

The present invention is directed to methods for treating bioprosthetic tissue for implantation in a patient and, more particularly, to methods for capping and/or crosslinking bioprosthetic tissue using a nucleophile and/or an electrophile in a catalytic system.

BACKGROUND

Significant challenges are presented by the use of non-autologous tissue in bioprosthetic implants. Chief among the challenges are preventing immunological rejection of the bioprosthetic implant by the host and calcification of the tissue, which results in the undesirable stiffening and degradation of the tissue. Immunological rejection and calcification are particularly problematic for bioprosthetic heart valves, as calcification of valve leaflets after implantation will adversely affect its ability to maintain a one-way flow of blood and prevent undesirable leaking or regurgitation of blood.

Glutaraldehyde has long been the reagent of choice for fixing and sterilizing tissue intended for bioprosthetic implants. The use of glutaraldehyde for fixing bioprosthetic tissue, however, has many significant disadvantages. Because glutaraldehyde tends to polymerize in solution, glutaraldehyde-fixed tissues are often characterized as having residual aldehyde groups associated with the fixed tissue.

Additionally, glutaraldehyde reacts with the free amines in the tissue to generate labile Schiff bases. Both the residual aldehydes and Schiff bases in glutaraldehyde-fixed tissues represent potential calcium binding sites that may lead to in viva calcification. Moreover, because glutaraldehyde is cytotoxic, it inhibits the desired cellular in-growth and integration of the implanted and glutaraldehyde-treated bioprosthetic tissue.

What is therefore needed are strategies that may be used in place of, or in conjunction with, glutaraldehyde fixation for mitigating some of the undesirable interactions between implanted bioprosthetic tissue and the host.

BRIEF SUMMARY

Described herein are processes for altering functional groups on biological tissues which represent actual and potential calcium binding sites and also processes for crosslinking bioprosthetic tissue. Both these processes can be used in conjunction with known fixative techniques, such as glutaraldehyde fixation, or can be used to replace known fixative techniques.

In one embodiment, a method for treating a bioprosthetic tissue is provided. The method comprises contacting the bioprosthetic tissue with one of a nucleophile or an electrophile in the presence of a catalytic system. The catalytic system comprises at least one or a combination of a fluoride-based salt, a cesium-based salt, a potassium-based salt, a rubidium-based salt, and a carbonate-based salt.

In accordance with a first aspect, the contacting is performed with a nucleophile. The nucleophile comprises one or more functional groups selected from the group consisting of: an amine, a hydroxyl and a sulfhydryl.

In accordance with a second aspect, the nucleophile is 2-mercaptoethanol, ethanolamine or a combination thereof.

In accordance with a third aspect, the nucleophile comprises one or a combination of polyamines, polyols and polythiols.

In accordance with a fourth aspect, the polyamines comprise one or more selected from the group consisting of: cystamine, ethylenediamine, 1,3-diaminopropane, putrescine, cadaverine, and hexamethylenediamine.

In accordance with a fifth aspect, the polyols comprise one or more selected from the group consisting of ethylene glycol, 1,3-propanediol, 1,4-butanediol, 1,5-pentanediol, and octane-1,8-diol.

In accordance with a sixth aspect, the contacting is performed with an electrophile. The electrophile comprises one or more carbonyl functional groups.

In accordance with a seventh aspect, the electrophile comprises one or both of a polyaldehyde and a polycarboxylic acid. The polyaldehyde is selected from the group consisting of: glutaraldehyde, glyoxal, malondialdehyde, and succinaldehyde. The polycarboxylic acid is selected from the group consisting of oxalic acid, malonic acid, succinic acid, glutaric acid, adipic acid, pimelic acid, suberic acid, azelaic acid, sebacic acid, aconitic acid, propane-1,2, 3-tricarboxylic acid, and 5-oxopentanoic acid.

In accordance with an eighth aspect, the catalytic system further comprises at least one pyridinium salt.

In accordance with a ninth aspect, the pyridinium salt comprises one or more selected from the group consisting of: 2-fluoro-1-methylpyridinium p-toluenesulfonate (FMPTS), 2-fluoro-1-ethylpyridinium p-toluenesulfonate (FEPTS), 2-chloro-1-methylpyridinium p-toluenesulfonate (CEPTS), and 2-chloro-1-methylpyridinium iodide (CMPI).

In accordance with a tenth aspect, the catalytic system comprises FMPTS and CsF.

In accordance with an eleventh aspect, the catalytic system comprises one or both of the fluoride-based salt and the carbonate-based salt.

In accordance with a twelfth aspect, the fluoride-based salt is one or a combination of CsF, RbF and KF.

In accordance with a thirteenth aspect, the cesium-based salt is one or a combination of CsF and $Cs_2CO_3$.

In accordance with a fourteenth aspect, the potassium-based salt is one or a combination of KF and $K_2CO_3$.

In accordance with a fifteenth aspect, the rubidium-based salt is one or a combination of RbF and $Rb_2CO_3$.

In accordance with a sixteenth aspect, the contacting is performed in a solvent system. The solvent system comprises one or more selected from the group consisting of: an alcohol, a nitrile, a ketone, an ester, an amide, a sulfoxide, an ether, a cyclic ether, a lactone, and a lactam.

In accordance with a seventeenth aspect, the solvent system comprises one or more selected from the group consisting of: acetonitrile, butyl acetate, ethyl acetate, N,N-dimethylformamide (DMF), dimethyl sulfoxide (DMSO), 1,4-dioxane, glycerol, 3-methyl-1-butanol, 1-methyl-2-pyrrolidinone, pyridine, tetrahydrofuran (THF), and diglyme.

In accordance with an eighteenth aspect, the contacting is performed in a solvent system comprising glycerol and ethanol.

In accordance with a nineteenth aspect, the contacting is performed in a solvent system comprising one or more selected from the group consisting of: water, saline, phosphate-buffered saline (PBS), buffers having a pH of 1-13, and mixtures of organic solvents with water or buffers having a pH of 1-13.

In accordance with a twentieth aspect, the contacting is performed with a nucleophile in the presence of a solvent system, wherein the nucleophile is cystamine, wherein the catalytic system comprises CsF and FMPTS, and wherein the solvent system comprises DMSO or glycerol and ethanol.

In accordance with a twenty-first aspect, the contacting is performed with a nucleophile in the presence of a solvent system, wherein the nucleophile is cystamine, wherein the catalytic system comprises CsF and FMPTS, and wherein the solvent system comprises a buffered aqueous solution.

Other objects, features and advantages of the described preferred embodiments will become apparent to those skilled in the art from the following detailed description. It is to be understood, however, that the detailed description and specific examples, while indicating preferred embodiments, are given by way of illustration and not limitation. Many changes and modifications within the scope of the present disclosure can be made without departing from the spirit thereof, and the disclosure includes all such modifications.

BRIEF DESCRIPTION OF THE DRAWINGS

Illustrative embodiments of the present disclosure are described herein with reference to the accompanying drawings, in which.

DETAILED DESCRIPTION OF THE PREFERRED EMBODIMENTS

Specific, non-limiting embodiments of the methods for cross-linking bioprosthetic tissue will now be described with reference to the drawings. It should be understood that such embodiments are by way of example only and merely illustrative of but a small number of embodiments within the scope of the present disclosure. Various changes and modifications obvious to one skilled in the art to which the present disclosure pertains are deemed to be within the spirit, scope and contemplation of the present disclosure as further defined in the appended claims.

The preferred embodiments described herein are directed to methods for treating biological tissue for use in connection with an implantable bioprosthesis. Because biological tissues used for implantable bioprostheses originate from non-autologous sources, the biological tissue must be treated prior to implantation to maintain a sufficient degree of mechanical strength and dimensional stability. At the same time, the biological tissue must also be treated to reduce its antigenicity in the patient and to reduce actual and potential binding sites for calcium. The biological tissue can be derived from animal sources, such as from pericardial tissue, and in particular, from bovine pericardial tissue.

Fixation Process. In one preferred embodiment, the biological tissue can be subjected to a fixation process, as a result of which the biological tissue is rendered less antigenic and is at least partially or completely cross-linked. The fixation process is understood to include any chemical, heat or other processes as a result of which the biological tissue is preserved and rendered mechanically and dimensionally stable.

The fixation process can include contacting the tissue with one or more fixatives. Known fixatives include aldehydes, polyaldehydes, diisocyanates, carbodiimides, photooxidation agents, and polyepoxide compounds. In a preferred embodiment, the fixative used is glutaraldehyde. Glutaraldehyde-fixed tissue, however, is particularly vulnerable to calcification since glutaraldehyde fixation results in the generation of residual aldehyde groups and labile Schiff bases. The residual aldehydes and Schiff bases are potential binding sites for calcium. The aldehyde groups may oxidize to carboxylic acid groups, which are known to attract and bind calcium.

Various techniques have therefore been developed to reduce the aldehyde and acid levels of glutaraldehyde-fixed tissues, and thus to its propensity to calcify after implantation in the patient.

The fixation process can include adjusting the pH of the glutaraldehyde fixative in solution to reduce the generation of calcium binding sites, as disclosed in U.S. Pat. No. 6,878,168 to Edwards Lifesciences, the entire contents of which are incorporated herein by reference.

The fixation process can also further include the addition of a heat-treating step after contacting with the one or more fixatives. Glutaraldehyde-fixed tissue have demonstrated a reduced aldehyde and carboxylic acid content after heat treatment, and thus a marked reduction in calcification after implantation, as compared to glutaraldehyde-fixed tissue without heat treatment. Heat treatment of glutaraldehyde-fixed tissue is described in U.S. Pat. No. 6,561,970, issued May 13, 2003 to Edwards Lifesciences, the entire contents of which are incorporated herein by reference. The heat treatment of glutaraldehyde-fixed tissue is also commercially known as the Carpentier-Edwards ThermaFix® (TFX) tissue treatment process from Edwards Lifesciences.

The fixation process can also further include subjecting the biological tissue to pre-conditioning, pre-stressing or pre-damaging fixed tissue to generate additional acid binding sites which can subsequently be capped, as described in U.S. Pub. No. 2008/0302372, entitled "Methods for Pre-Stressing and Capping Bioprosthetic Tissue" to Edwards Lifesciences, the entire contents of which are incorporated herein by reference.

The fixation process can be preceded by, followed by, or replaced by one or both of a treatment with a nucleophile and/or an electrophile in a catalytic system. Among the advantages of selecting and utilizing one or a combination of nucleophiles and/or electrophiles described herein is that it permits either one or both of the capping or cross-linking of the bioprosthetic tissue based on any one or a combination of the different tissue functional groups, including aldehydes, carboxylic acids, amines, hydroxyls, and sulfhydryl groups.

The terms "cap" or "capping" refers to the blocking, removal, or alteration of a functional group that actually or potentially produces an undesirable interaction between the implanted biological tissue and the host, such as calcification, an immunological rejection, etc.

The terms "cross-link" or "cross-linking" refers to the coupling or formation of covalent bonds between proteins in the bioprosthetic tissue directly via known agents, such as glutaraldehyde, or via the nucleophiles and/or electrophiles disclosed herein. For example, the polyfunctional nucleophiles or electrophiles described herein can form covalent bonds with the functional groups of the amino acid residues of collagenous tissue.

As the relative number of the different functional groups (i.e., aldehydes, carboxylic acids, amines, hydroxyls and sulfhydryl groups) in a bioprosthetic tissue necessarily differs, the nucleophilic and/or electrophilic treatment methods permit the bioprosthetic tissue to be variably cross-linked based on the selection of the particular nucleophile and/or electrophile and the extent to which the tissue functional groups targeted by the selected nucleophile and/or electrophile are present in the bioprosthetic tissue. The combination of the nucleophiles and/or electrophiles, the catalytic system and the solvent system provides significantly improved reaction efficiency with respect to the various functional groups associated with the bioprosthetic tissue that are capped, crosslinked or both.

In accordance with one embodiment, a method for capping and/or cross-linking aldehyde and carboxylic acid functional groups in a bioprosthetic tissue is provided. The method comprises treating the bioprosthetic tissue with a polyfunctional agent in the presence of a catalytic system in a solvent system. The polyfunctional agent preferably comprises at least two functional groups selected from the group consisting of: aldehydes, carboxylic acids, amines, hydroxyls, and sulfhydryls. The catalytic system preferably comprises at least one pyridinium salt and at least one or a combination of a fluoride-based salt, a cesium-based salt, a potassium-based salt, a rubidium-based salt, and a carbonate-based salt.

Treatment with Nucleophile in a Catalytic System. Prior to, subsequent to or in place of the traditional fixation processes described above (e.g., glutaraldehyde fixation), the bioprosthetic tissue can be contacted with at least one nucleophile in the presence of a catalytic system, preferably in a solvent system. The nucleophile can react with one or a combination of aldehyde or carboxylic acid groups associated with the bioprosthetic tissue. The catalytic system comprises at least one fluoride-based salt, a cesium-based salt or a carbonate-based salt. In a particularly preferred embodiment, the catalytic system further comprises at least one pyridinium salt. The catalytic system is believed to significantly improve the efficiency of the reaction between the nucleophile, on the one hand, and the free aldehydes and/or carboxylic acid groups associated with the bioprosthetic tissue, on the other hand. This, in turn, increases the extent to which the aldehyde and carboxylic acid groups are capped, cross-linked, or both, depending on the type of nucleophile used in the process.

In a preferred embodiment, the nucleophile can comprise one or more functional groups selected from an amine, a hydroxyl and a sulfhydryl, such that the nucleophile can be an amine, an alcohol, a thiol, or compound with heterogenous functional groups.

In one preferred embodiment, the nucleophile is 2-mercaptoethanol, ethanolamine or a combination thereof.

For purposes of capping, the nucleophile preferably comprises at least one functional group that is capable of reacting with the aldehyde and/or carboxylic acid groups associated with the bioprosthetic tissue.

The location of the functional group(s) on the nucleophile is preferably a terminal position or a non-terminal position that is not sterically hindered from reacting with the aldehyde and carboxylic acid groups associated with the bioprosthetic tissue. The nucleophile can also comprise more than one functional group and thus can be a polyamine, polyol or a polysulfhydryl to enhance the capping efficiency of the nucleophile.

In one preferred embodiment, the polyamine is one or more of cystamine, ethylenediamine, 1,3-diaminopropane, putrescine, cadaverine, and hexamethylenediamine.

In another preferred embodiment, the polyol is one or more of ethylene glycol, 1,3-propanediol, 1,4-butanediol, 1,5-pentanediol, and octane-1,8-diol.

For the additional purpose of achieving at least a partial cross-linking of the tissue, the nucleophile preferably comprises two or more functional groups such that a single nucleophile is capable of reacting with at least two aldehyde groups, at least two carboxylic acid groups or at least one aldehyde and at least one carboxylic acid groups associated with the bioprosthetic tissue. The two or more functional groups for a given nucleophile can be homogenous or heterogeneous and can also be selected from an amine, a hydroxyl and a sulfhydryl.

The nucleophile can have a straight or branched structure, with the functional groups preferably being located on the terminal portions of the straight or branched portions or be located in a position where the functional group is not sterically hindered from reacting with the aldehyde or carboxylic acid groups.

The functional groups can be separated by a length which corresponds to how closely adjacent collagen molecules are to be cross-linked. This, in turn, will affect the relative stiffness of the bioprosthetic tissue, with a short separation between functional groups giving rise to a stiffer tissue and a longer separation between functional groups giving rise to a more pliable or flexible tissue. Additional bio-functional molecules can further be provided within the nucleophile between or adjacent to the functional groups.

In one preferred embodiment, the nucleophile is a polyamine and, more particularly, a diamine having the formula:

$$NH_2-R_1-M_n-R_2-NH_2$$

wherein $R_1$ and $R_2$, independently of one another, is a straight or branched $C_1$-$C_{10}$ alkyl, an alkenyl, an alkynyl, and aryl, M is selected from S; and n is 0, 1, 2, 3, or 4.

In a particularly preferred embodiment, the polyamine is a cystamine. The functional group represented by M is such that it can impart additional properties to the nucleophile. Cystamine, for example, comprises a disulfide bond (e.g., wherein M is S and n is 2) which can be enzymatically cleaved, which in turn presents the ability to alter the extent to which the bioprosthetic tissue is cross-linked.

In accordance with one preferred embodiment, the bioprosthetic tissue is fixed with glutaraldehyde and subjected to one or a combination of heat and/or pH treatment as part of the fixation process. The glutaraldehyde-fixed bioprosthetic tissue is then exposed to a combination of cystamine and a catalytic system in a solvent system. The catalytic system can preferably comprise FMPTS and cesium fluoride. The solvent system can be one of a DMSO solution (non-aqueous), a combination of glycerol and ethanol (non-aqueous), or a phosphate-buffered saline solution (aqueous).

Figure 1:
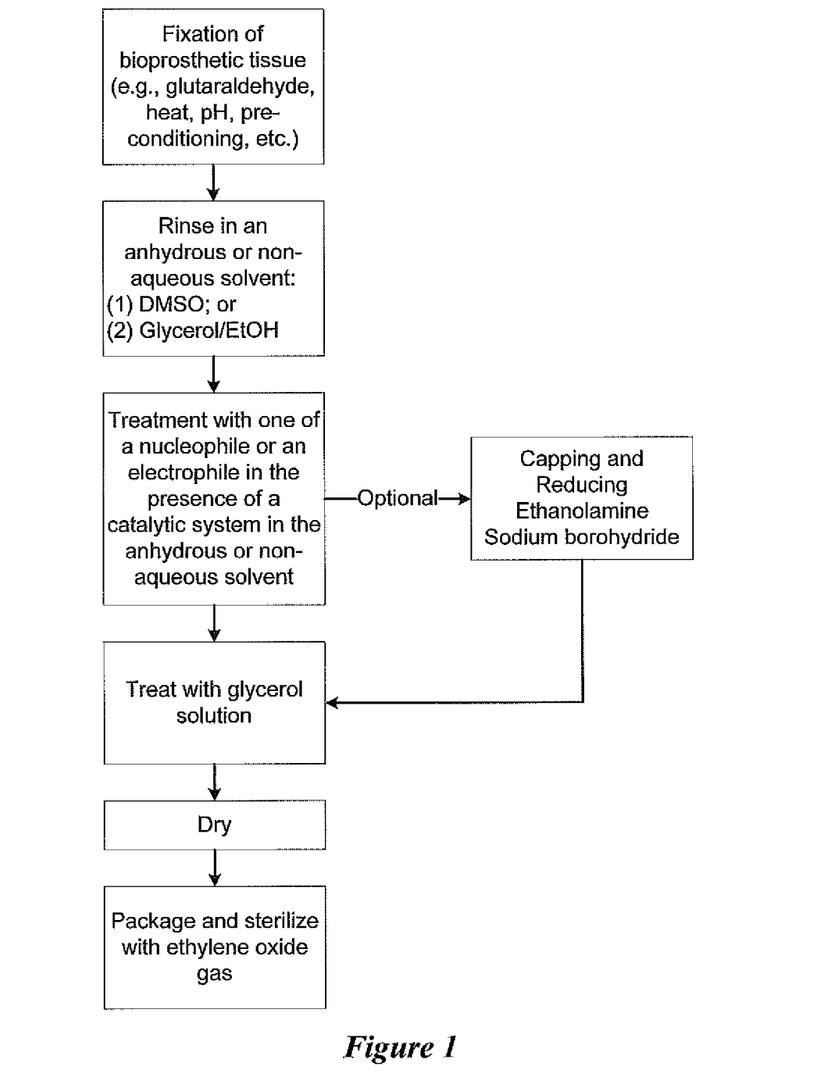
FIG. 1 is a flow chart of an exemplary process for cross-linking and capping bioprosthetic tissue in either an anhydrous or a non-aqueous solvent system.
Figure 2:
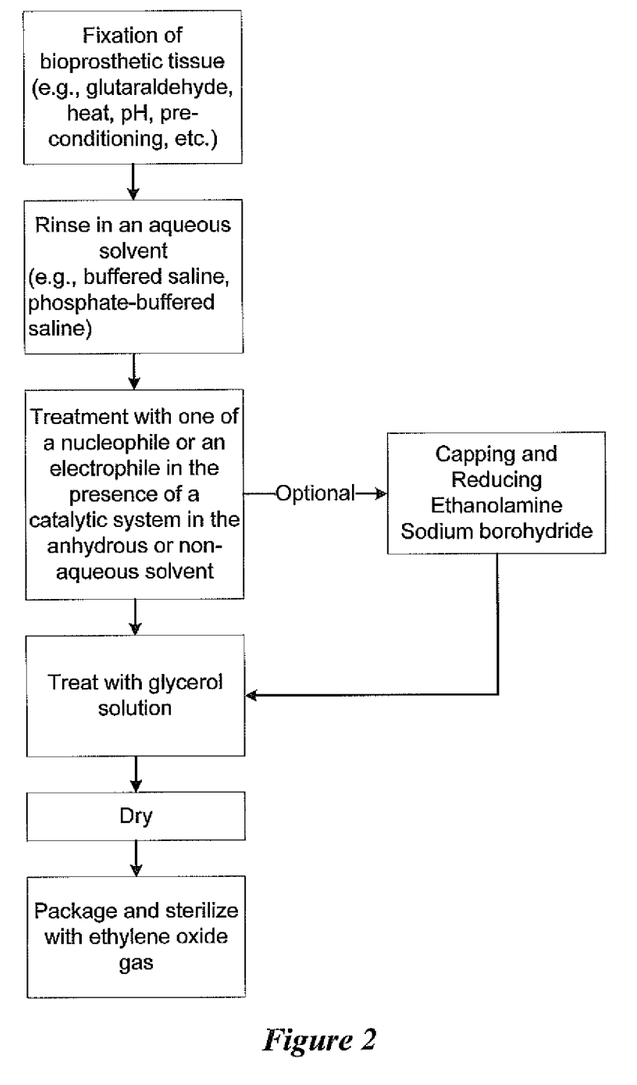
FIG. 2 is a flow chart of an exemplary process for cross-linking and capping bioprosthetic tissue in an aqueous solvent system.

FIG. 1 depicts exemplary steps of the methods described herein, with FIG. 1 describing the nucleophilic/electrophilic treatment processes in either an anhydrous or alternatively a non-aqueous solvent system and FIG. 2 describing the nucleophilic/electrophilic treatment processes in connection with an aqueous solvent system. It is noted that in either of the processes described in FIGS. 1 and 2, the fixation step and the capping and reduction steps with ethanolamine and sodium borohydride, respectively, are not required but can be incorporated based on the objectives of the treatment processes.

For example, in embodiments where cross-linking of the tissue without the use of glutaraldehyde is desired, the fixation step can be omitted and the nucleophilic/electrophilic treatment can include use of a polyfunctional nucleophile or electrophile that is capable of establishing tissue cross-linkages by coupling functional groups associated with the tissue.

Moreover, the additional ethanolamine and sodium borohydride capping and reducing steps are not required; however, in the event that the electrophile or nucleophile chosen in the process results in the generation of free aldehyde groups, as may be the case where a polyfunctional electrophile having carbonyl groups is employed, the additional capping and reducing step with ethanolamine and sodium borohydride can ensure that free aldehyde groups present in the fixed tissue are adequately capped.

Treatment of the bioprosthetic tissue with the cystamine and the FMPTS/CsF catalytic system in one of the three solvent systems is believed to produce significant capping of aldehyde and carboxylic acid groups of the fixed tissue. The combination of cystamine, FMPTS/CsF in the DMSO solvent system has been demonstrated to be particularly effective in capping carboxylic acid groups and the combination of cystamine, FMPTS/CsF in the glycerol and ethanol solvent system or the phosphate-buffered saline solution has been demonstrated to be particularly effective in capping aldehyde groups in the bioprosthetic tissue.

Treatment with Electrophile in a Catalytic System. Alternatively or in addition to (either before or after) the above-described nucleophilic treatment, the bioprosthetic tissue can be subjected to a treatment with an electrophile in a catalytic system, also preferably in a solvent system. The electrophile can react with one or more of an amine group, a hydroxyl group or a sulfhydryl group associated with the bioprosthetic tissue. The catalytic system comprises at least one fluoride-based salt or a cesium-based salt or a carbonate-based salt. In a particularly preferred embodiment, the catalytic system further comprises at least one pyridinium salt. The catalytic system is believed to significantly improve the efficiency of the reaction between the electrophile, on the one hand, and the free amine, hydroxyl or sulfhydryl groups associated with the bioprosthetic tissue, on the other hand. This, in turn, increases the extent to which the amine, hydroxyl and sulfhydryl groups are capped, cross-linked, or both, depending on the type of electrophile used in the process.

In a preferred embodiment, the electrophile can comprise one or more functional groups selected from an aldehyde group and a carboxylic acid group. The electrophile can be an aldehyde or a carboxylic acid.

Alternatively, the electrophile can be a polyaldehyde, such as glutaraldehyde, glyoxal, malondialdehyde, and succinaldehyde, or a polycarboxylic acid, such as oxalic acid, malonic acid, succinic acid, glutaric acid, adipic acid, pimelic acid, suberic acid, azelaic acid, sebacic acid, aconitic acid, propane-1,2,3-tricarboxylic acid, and 5-oxopentanoic acid.

For purposes of capping, the electrophile preferably comprises at least one functional group that is capable of reacting with the amine, hydroxyl and sulfhydryl groups associated with the bioprosthetic tissue. Thus, the location of the functional group(s) of the electrophile is preferably a terminal group or a non-terminal group that is not sterically hindered from reacting with the amine, hydroxyl and/or sulfhydryl groups associated with the bioprosthetic tissue.

For the additional purpose of achieving at least a partial cross-linking of the tissue, the electrophile preferably comprises two or more functional groups such that a single electrophile is capable of reacting with at least two functional groups associated with the bioprosthetic tissue. Each one of the two functional groups can be selected from the group consisting of aldehyde and carboxylic acid groups and a given electrophile can comprise heterogeneous or homogenous functional groups.

The electrophile can have a straight or branched structure, with the functional groups preferably being located on the terminal portions of the straight or branched portions or being located in a position where the functional group is not sterically hindered from reacting with the amine, hydroxyl, and sulfhydryl groups on the tissue. The functional groups can be separated by a length which corresponds to how closely adjacent collagen molecules are to be cross-linked. This, in turn, will affect the relative stiffness of the bioprosthetic tissue, with a short separation between functional groups giving rise to a stiffer tissue and a longer separation between functional groups giving rise to a more pliable or flexible tissue. Additional bio-functional molecules can further be provided within the nucleophile between or adjacent to the functional groups.

Catalytic System. As discussed above with respect to the nucleophilic and electrophilic treatment processes, the catalytic system comprises at least one or a combination of a fluoride-based salt, a cesium-based salt, a potassium-based salt, a rubidium-based salt, and a carbonate-based salt. The catalytic system can additionally comprise one or a combination of pyridinium-based salts.

It is believed that the use of the catalytic system significantly increases the nucleophilic and/or electrophilic reaction efficiency such that it provides a greater degree of predictability as to the extent of the capping and/or cross-linking of the bioprosthetic tissue. While a combination of at least one of a fluoride-based salt, cesium-based salt potassium-based salt, rubidium-based salt, or a carbonate-based salt with a pyridinium-based salt produces superior nucleophilic and/or electrophilic reaction efficiency, it is understood that the catalytic system can also comprise only one of the foregoing catalysts to produce partial capping and/or cross-linking of the bioprosthetic tissue by either one or both of the nucleophile(s) and/or the electrophile(s).

In a preferred embodiment, the catalytic system comprises one or both of the fluoride-based salt and the carbonate-based salt.

In another preferred embodiment, the fluoride-based salt can be one or a combination of cesium fluoride (CsF), potassium fluoride (KF), and rubidium fluoride (RbF).

In yet another preferred embodiment, the cesium-based salt can be one or a combination of CsF and cesium carbonate ($Cs_2CO_3$).

In a further preferred embodiment, the potassium-based salt can be one or a combination of KF and potassium carbonate ($K_2CO_3$).

In yet another preferred embodiment, the rubidium-based salt can be one or a combination of RbF or $Rb_2CO_3$.

In yet a further preferred embodiment, the pyridinium salt can comprise one or a combination of 2-fluoro-1-methyl-pyridinium p-toluenesulfonate (FMPTS), 2-fluoro-1-ethyl-pyridinium p-toluenesulfonate (FEPTS), 2-chloro-1-methylpyridinium p-toluenesulfonate (CEPTS), and 2-chloro-1-methylpyridinium iodide (CMPI).

In a particularly preferred embodiment, the catalytic system comprises FMPTS and CsF. Alternatively, rubidium and potassium-based catalysts can additionally be included in the catalytic system.

Solvent System. The solvent system is further believed to contribute to the reaction efficiency of the electrophile(s)/nucleophile(s) with the tissue functional groups. The solvent system can be an anhydrous, non-aqueous or an aqueous system.

The term "non-aqueous," as it refers to the solvent system, is understood to mean a solvent system in which less than 50% by weight of the solvent system is water. Thus, a non-aqueous solvent system does not exclude the presence of water, either as an impurity or in amounts less than 50% by weight. It is further understood that where the methods are disclosed as utilizing anhydrous solvent systems, corresponding non-aqueous solutions may be substituted for anhydrous solutions.

In a preferred embodiment, the solvent system includes one or a combination of an alcohol, a nitrile, a ketone, an ester, an amide, a sulfoxide, an ether, a cyclic ether, a lactone, and a lactam.

The anhydrous or non-aqueous solvent can comprise one or a combination of alcohol ($C_nH_{2n+1}OH$), acetonitrile, butyl acetate, ethyl acetate, N,N-dimethylformamide (DMF), dimethyl sulfoxide (DMSO), 1,4-dioxane, glycerol, 3-methyl-1-butanol, 1-methyl-2-pyrrolidinone, pyridine, tetrahydrofuran (THF), and diglyme. In a preferred embodiment, the solvent system comprises one or a combination of glycerol, alcohol and dimethylsulfoxide (DMSO).

The aqueous solvent can comprise a saline solution, preferably a buffered aqueous or saline solution or one or a combination of water, 0.9% saline, phosphate-buffered saline (PBS), any buffers having a pH of 1 to 13, and mixtures of any organic solvents with water or buffers having a pH of 1 to 13.

Treatment with Capping and/or Reducing Agents. Following the processes of fixation, the treatment with the nucleophile, electrophile, or both, as described above, the process can further comprise a treatment with a capping and reducing agent. Insofar as the reaction of aldehydes and amines result in the formation of labile Schiff bases, it is desirable to reduce the Schiff base and replace it with a more stabile amine.

Moreover, insofar as residual aldehydes can be present in the tissue following the processes of fixation and/or treatment with the nucleophiles or electrophiles, the bioprosthetic tissue can be subjected to a further capping process by contacting the tissue with ethanolamine and a reducing agent. In a preferred embodiment, the reducing agent is sodium borohydride. Exemplary capping and reducing agents and processes are described in U.S. Pat. No. 7,972,376, the entire contents of which are incorporated by reference as if fully set forth herein.

Oxidation of Residual Aldehydes. As an alternative to the treatment with reducing agent described above, residual aldehydes can also be oxidized to carboxylic acids and the carboxylic acids can be reacted with an ethanolamine to produce a more stable peptide bond and to cap the carboxylic acids with an alcohol. The carboxylic acid groups associated with the bioprosthetic tissue can also be capped or cross-linked by the nucleophilic or electrophilic treatment, as described above.

Glycerol Treatment. The bioprosthetic tissue can further undergo treatment with anhydrous, non-aqueous or aqueous solutions to substantially, if not completely, dehydrate the bioprosthetic tissue for dry storage.

In a preferred embodiment, the anhydrous or non-aqueous solution comprises glycerol and, more preferably, a solution of 75 wt % glycerol and 25 wt % ethanol, and the bioprosthetic tissue is soaked in the glycerol solution for at least one hour. The bioprosthetic tissue is then removed and placed in a clean hood to allow removal of excess solution.

In a preferred embodiment, the anhydrous or non-aqueous solution is a solution of glycerol and a $C_1$-$C_3$ alcohol, wherein the treatment solution comprises 60-95% by volume glycerol. Suitable treatments for the biological tissues are described in U.S. Pat. No. 8,007,992, issued Aug. 30, 2011, to Edwards Lifesciences Corp., the entire contents of which are incorporated herein by reference as if fully set forth herein.

In another preferred embodiment, an aqueous glycerol solution can be used to at least partially dehydrate the tissue, as described in U.S. Pat. No. 6,534,004, issued Mar. 18, 2003, issued to The Cleveland Clinic Foundation, the entire contents of which are incorporated herein by reference in its entirety as if fully set forth herein.

The terms "dry" or "dehydrated," as used herein, are understood to include residual treatment solution or moisture or humidity from the ambient environment following treatment with the anhydrous, non-aqueous or aqueous glycerol solutions.

Ethylene Oxide Sterilization. The dehydrated bioprosthetic tissue is provided in a sealed package, preferably in a double sterile barrier packaging consisting of a rigid tray (PETG) with a Tyvek lid. The package is sealed in a clean room, and sterilized in 100% ethylene oxide.

It is to be understood that the detailed description and specific examples, while indicating preferred embodiments of the present disclosure, are given by way of illustration and not limitation. Many changes and modifications within the scope of the present disclosure may be made without departing from the spirit thereof, and the disclosure includes all such modifications.

What is claimed is:

1. A method for treating a bioprosthetic tissue comprising:
   contacting the bioprosthetic tissue with a nucleophile in the presence of a catalytic system to at least partially cross-link the bioprosthetic tissue;
   wherein the nucleophile directly reacts with tissue functional groups associated with the bioprosthetic tissue, and wherein the nucleophile comprises cystamine;
   wherein the catalytic system comprises at least one or a combination of a fluoride-based salt, a cesium-based salt, a potassium-based salt, or a rubidium-based salt;
   wherein the bioprosthetic tissue is not treated with a glutaraldehyde to at least partially cross-link the bioprosthetic tissue; and
   wherein the bioprosthetic tissue has reduced antigenicity and reduced binding sites for calcium after implantation.

2. The method of claim 1, wherein the catalytic system further comprises at least one pyridinium salt.

3. The method of claim 2, wherein the pyridinium salt comprises one or more selected from the group consisting of: 2-fluoro-1-methylpyridinium p-toluenesulfonate (FMPTS), 2-fluoro-1-ethylpyridinium p-toluenesulfonate (FEPTS), 2-chloro-1-methylpyridinium p-toluenesulfonate (CEPTS), and 2-chloro-1-methylpyridinium iodide (CMPI).

4. The method of claim 3, wherein the catalytic system comprises FMPTS and CsF.

5. The method of claim 1, wherein the catalytic system comprises one or both of the fluoride-based salt and the carbonate based salt.

6. The method of claim 1, wherein the fluoride-based salt is one or a combination of CsF, RbF and KF.

7. The method of claim 1, wherein the cesium-based salt is one or a combination of CsF and $Cs_2CO_3$.

8. The method of claim 1, wherein the potassium-based salt is one or a combination of KF and $K_2CO_3$.

9. The method of claim 1, wherein the rubidium-based salt is one or a combination of RbF and $Rb_2CO_3$.

10. The method of claim 1, wherein the contacting is performed in a solvent system, and wherein the solvent system comprises one or more selected from the group consisting of: an alcohol, a nitrile, a ketone, an ester, an amide, a sulfoxide, an ether, a cyclic ether, a lactone, and a lactam.

11. The method of claim 10, wherein the solvent system comprises one or more selected from the group consisting of: acetonitrile, butyl acetate, ethyl acetate, N,N-dimethylformamide (DMF), dimethyl sulfoxide (DMSO), 1,4-dioxane, glycerol, 3-methyl-1-mutanol, 1-methyl-2-pyrrolidinone, pyridine, tetrahydrofuran (THF), and diglyme.

12. The method of claim 1, wherein the contacting is performed in a solvent system comprising glycerol and ethanol.

13. The method of claim 1, wherein the contacting is performed in a solvent system comprising one or more selected from the group consisting of: water, saline, phosphate-buffered saline (PBS), buffers having a pH of 1-13, and mixtures of organic solvents with water or buffers having a pH of 1-13.

14. The method of claim 1, wherein the catalytic system comprises CsF and FMPTS; and wherein the contacting is performed in a solvent system comprising DMSO or glycerol and ethanol.

15. The method of claim 1, wherein the catalytic system comprises CsF and FMPTS; and wherein the contacting is performed in a solvent system comprising a buffered aqueous solution.

16. The method of claim 1, further comprising treating the bioprosthetic tissue with glycerol.

17. The method of claim 16, wherein the bioprosthetic tissue is treated with glycerol after the bioprosthetic tissue is contacted with the nucleophile in the presence of the catalytic system.

* * * * *